(12) United States Patent
Shirer

(10) Patent No.: US 6,444,282 B1
(45) Date of Patent: Sep. 3, 2002

(54) METHOD AND APPARATUS FOR FORMING A PROSTHETIC SOCKET

(75) Inventor: Lee A. Shirer, 1646 Burr Oak, Homewood, IL (US) 60430

(73) Assignee: Lee A. Shirer, Homewood, IL (US)

( * ) Notice: Subject to any disclaimer, the term of this patent is extended or adjusted under 35 U.S.C. 154(b) by 0 days.

(21) Appl. No.: 09/475,724

(22) Filed: Dec. 30, 1999

(51) Int. Cl.$^7$ ................................. A61F 2/76
(52) U.S. Cl. .................... 428/35.7; 428/542.8; 623/901
(58) Field of Search ............................ 428/35.7, 542.8; 623/36, 33, 38, 37, 901

(56) References Cited

U.S. PATENT DOCUMENTS

| | | | | |
|---|---|---|---|---|
| 4,498,827 A | * | 2/1985 | Mair | 411/349 |
| 5,201,775 A | * | 4/1993 | Arbogast et al. | 623/38 |
| 5,336,270 A | | 8/1994 | Lloyd | 623/33 |
| 5,376,127 A | | 12/1994 | Swanson | 623/27 |
| 5,884,625 A | * | 3/1999 | Hart | 128/207.14 |
| 5,888,231 A | | 3/1999 | Sandvig et al. | 623/36 |

FOREIGN PATENT DOCUMENTS

| | | |
|---|---|---|
| GB | 2 116 432 A | 9/1983 |
| GB | 2 149 309 A | 6/1985 |

OTHER PUBLICATIONS

European Search Report for Application No. EP 00 12 8722.

* cited by examiner

Primary Examiner—Shrive P. Beck
Assistant Examiner—Elena Tsoy
(74) Attorney, Agent, or Firm—Marshall Gerstein Borun

(57) ABSTRACT

A method and apparatus for forming an impression of a socket used in a prosthetic device. The impression is formed using a blank formed of a material which is malleable at low temperatures. The blank is inserted inside the socket and heated so that the blank assumes a molded shape which conforms to the shape and size of the socket. The molded blank is then cooled and removed from the socket. The blank material has a sufficient flexibility to allow the molded blank to deflect or bend significantly during removal yet return to its molded shape. The molded blank may then be used to form a new socket.

5 Claims, 2 Drawing Sheets

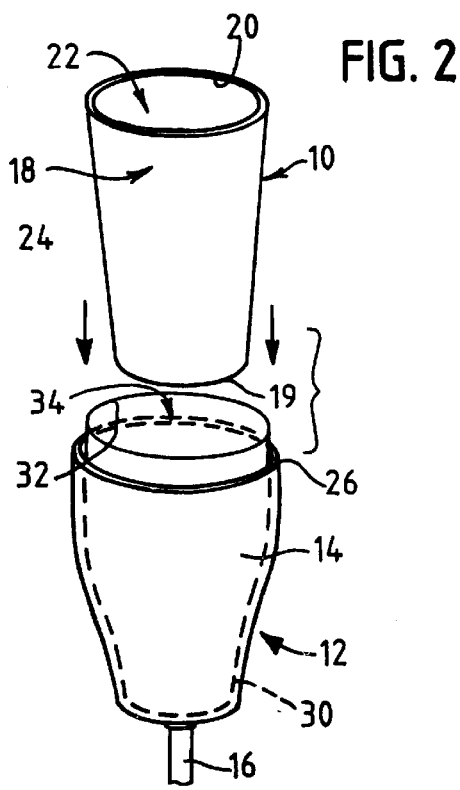
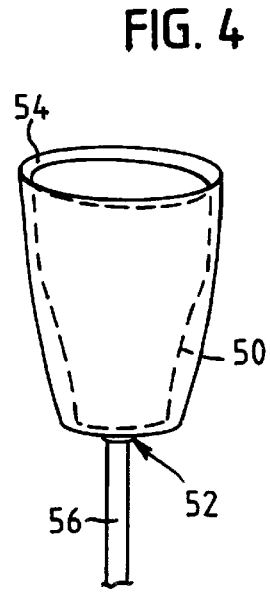
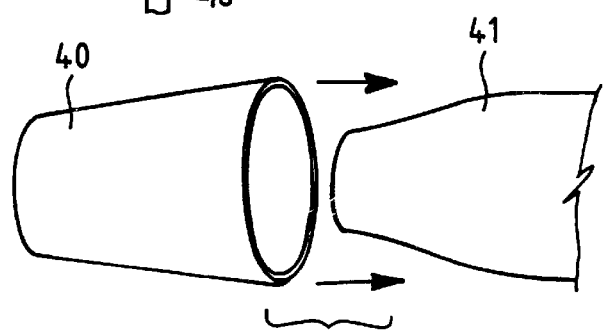
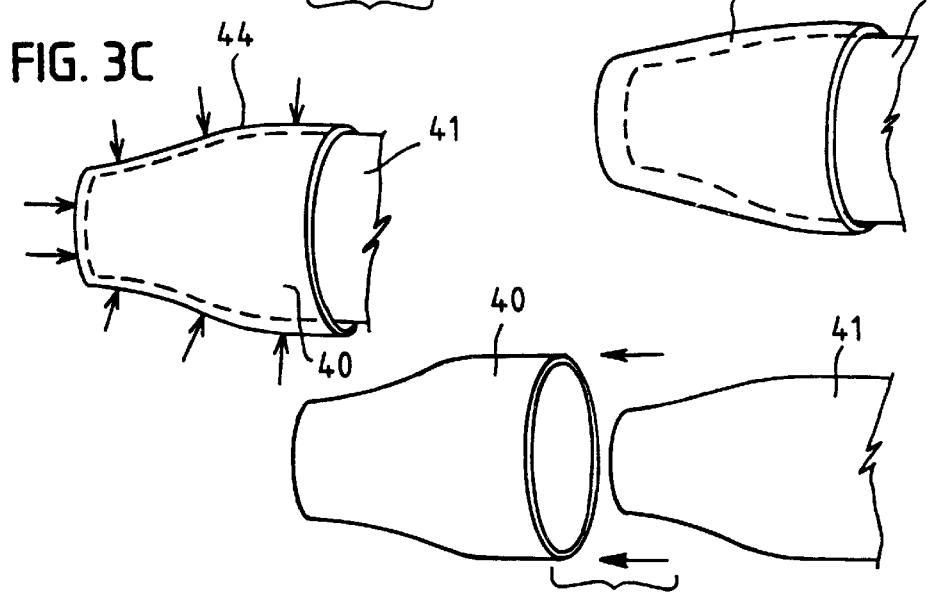

METHOD AND APPARATUS FOR FORMING A PROSTHETIC SOCKET

FIELD OF THE INVENTION

The present invention generally relates to prosthetic devices, and more particularly to methods and apparatus for forming prosthetic sockets.

BACKGROUND OF THE INVENTION

Prosthetic devices, such as artificial limbs, typically include a socket into which the remaining portion of a limb is inserted. The socket typically comprises a cup-shaped wall defining a recess into which the remaining portion of the limb is inserted. The socket may be formed by a single piece of rigid material, or may be a composite structure in which a more flexible liner is inserted inside a more rigid outer housing. In either event, several visits to a prosthetist are often needed, during which the shape and/or size of the socket is adjusted, to obtain a socket that fits the limb. Ultimately, a snug fit between the socket and the remaining portion of the limb is desired to maximize comfort to the user.

Unfortunately, several factors may contribute to deteriorate the fit of the socket. Atrophy of the remaining limb portion is a significant factor which contributes to deterioration of socket fit. Atrophy is typically greatest during the initial years of prosthetic use, and often necessitates up to five or more socket re-fittings and adjustments during the first two years. In addition, sockets are typically formed out of a plastic material which is subject to wear. As a result, the other components of the artificial limb typically last much longer than the socket and, therefore, several socket replacements may be required over the life of an artificial limb.

A new socket is typically fabricated using an impression of the original socket. The new socket is formed around the impression, so that the new socket has roughly the same size and shape as the original socket. Previously known methods and apparatus for making a socket impression, however, are overly costly and time consuming, and can introduce inaccuracies and imperfections in the socket duplication process.

For example, a direct plaster method is known in which the original socket is filled with plaster to form a positive plaster impression. The positive plaster impression is then removed from the original socket and used to form a new socket. The shape and geometry of the socket, however, often makes it necessary to cut or otherwise destroy the original socket to remove the positive plaster impression, which is not only wasteful but renders the prosthetic device useless until the replacement socket can be formed. In addition, the plaster must often be repaired, smoothed, and sealed before the new socket can be formed over the positive impression.

Another known method for making a socket impression is the direct plastic approach. In this method, the socket is first treated with a release agent, which is typically messy and generates an undesirable odor as a solvent used with the release agent evaporates. A two-part mixable plastic is poured into the socket, the plastic sets to form a plastic impression of the socket, and the plastic impression is then removed from the socket. The plastic material is flexible, which allows the plastic to be removed, often without requiring the original socket to be altered or otherwise taken apart. It is still difficult, however, to remove the plastic impression from the socket and, therefore, the plastic impression is susceptible to tearing and other deformations. This impression must then be filled with plaster, and a negative plaster wrap is taken and filled in order to create a positive plaster mold. The positive mold is then used to form the new socket. As a result, this method is overly costly and time consuming, and is susceptible to producing inaccuracies in the impression, especially since a second plaster impression is usually required.

A third known method for forming a socket impression is to fill the socket with alginate. The alginate is applied as a thick, viscous material which sets as a gel. The formed gel is then slipped out of the socket and wrapped with a plaster splint to create a positive mold of the socket impression. Plaster is then poured into the negative mold to form a plaster impression about which the new socket is formed. The alginate gel has not been found to accurately retain shape once it is removed from the original socket, and therefore the fit of a new socket formed using this method is often poor. In addition, the method is overly time consuming in that the formed gel is first used to create the positive mold, which is then used to form the plaster impression, before fabricating the new socket.

In each of the above methods, the original socket is coated or filled with a liquid or other flowable material. As a result, any holes or gaps in the original socket must be sealed. Furthermore, the flowable material may still leak through the holes, causing undue mess and requiring additional clean-up time.

While it is often desirable to form a new socket having the exact same size and shape as the original socket, there are many instances in which it is desirable to form a new socket having generally the same shape but a smaller size. As noted above, for example, the remaining portion of the limb may atrophy. To maintain a good fit with the original socket, the user of an artificial limb typically places one or more socks over the remaining portion of the limb to fill in the additional space. The socks must be kept clean and are often cumbersome to use. While a new socket which closely fits the smaller limb size would eliminate the additional gap, the fitting process is protracted and may cause discomfort until the proper adjustments are made. Furthermore, it is not seen how the above-described methods for forming socket impressions would be modified to accommodate the change in limb size.

SUMMARY OF THE INVENTION

In accordance with certain aspects of the present invention, a method of forming an impression of a prosthetic socket having an interior surface is provided in which a blank is used. The blank has a wall with an interior surface defining a recess and an exterior surface sized to fit the socket, and is formed of a material which is malleable under low heat and retains flexibility when subsequently cooled. The method comprises the steps of inserting the blank into the socket and heating the blank until the blank is sufficiently malleable. Pressure is exerted on the interior surface of the blank so that the exterior surface conforms to the interior surface of the socket, thereby forming the exterior surface with a molded shape corresponding to the interior surface of the socket. The blank is cooled and removed from the socket, whereby the flexibility of the material from which the blank is formed allows the exterior surface of the blank to deflect slightly during the removing step yet return to the molded shape.

In accordance with additional aspects of the present invention, a method of forming a reduced impression of a prosthetic socket having an interior surface is provided in which a blank is used. The blank has a wall defining an inner cavity and an exterior surface sized to fit the socket, and is formed of a material which is malleable under low heat and retains flexibility when subsequently cooled. The method comprises the steps of inserting a spacer into the socket, the spacer having an interior surface defining a reduced socket recess, and inserting the blank into the reduced socket recess. The blank is then heated until the exterior surface of the blank is sufficiently malleable, and pressure is exerted on the interior surface of the blank so that the exterior surface conforms to the interior surface of the spacer, thereby forming the exterior surface with a molded shape corresponding to the interior surface of the spacer. The blank is cooled and removed from the reduced socket recess. The flexibility of the material from which the blank is formed allows the exterior surface of the blank to deflect slightly during the removing step yet return to the molded shape.

In accordance with still further aspects of the present invention, a blank is provided for forming an impression of an interior surface of a prosthetic socket. The blank comprises a side wall having an exterior surface sized to fit inside the socket, and is formed of a thermoplastic material which is malleable when heated to a low temperature to allow the exterior surface of the side wall to be formed with a molded shape conforming to the interior surface of the socket. The side wall retains the molded shape when cooled, the thermoplastic material having a flexural modulus between approximately 40,000 to 250,000 psi to allow the side wall to temporarily deflect yet return to the molded shape, thereby allowing the blank to be removed from the socket.

BRIEF DESCRIPTION OF THE DRAWINGS

FIG. 2 is a perspective view similar to FIG. 1A showing a socket with a spacer inserted therein and an unmolded blank in accordance with certain aspects of the present invention.

FIG. 3A is a perspective view of a blank sized for insertion over a remaining limb portion, in accordance with certain aspects of the present invention.

FIG. 3B is a perspective view of the blank of FIG. 3A positioned over the remaining limb portion.

FIG. 3C is a perspective view of the blank as it is compressed to fit the contours of the remaining limb portion.

FIG. 3D is a perspective view of the molded blank as it is removed from the remaining limb portion.

FIG. 4 is a perspective view of a composite prosthetic device, in accordance with additional aspects of the present invention.

DETAILED DESCRIPTION OF THE PREFERRED EMBODIMENT

Figure 1A:
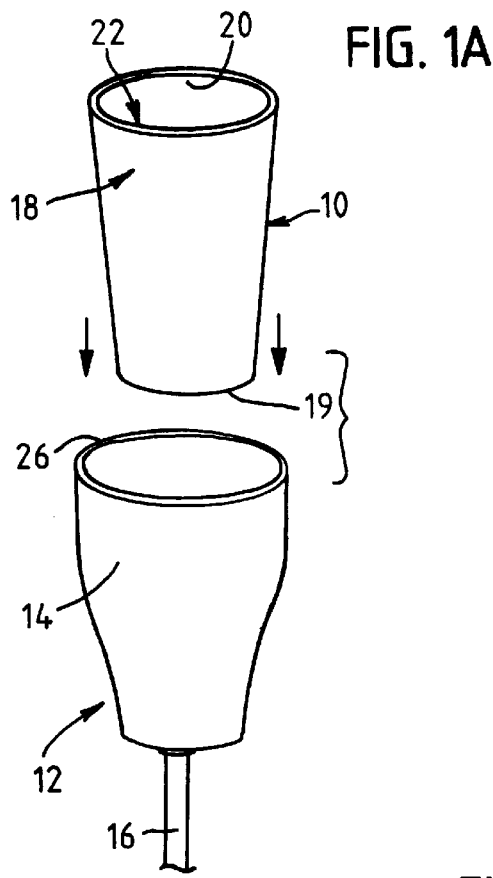
FIG. 1A is a perspective view of a prosthetic device having a socket and an unmolded blank sized for insertion into the socket, in accordance with the teachings of the present invention.

An unmolded blank constructed in accordance with the teachings of the present invention is generally indicated by reference numeral 10, as illustrated in FIG. 1A. The blank 10 is shown for use with a prosthetic device, such as an artificial leg 12. The artificial leg 12 has a socket 14 which receives the remaining portion of a user's limb. A supporting pylon 16 is attached to the socket 14 and extends to a foot section (not shown). The supporting pylon 16 and a portion of the socket 14 are typically enclosed in a cover (not shown) which has the appearance of a real leg. While for clarity of illustration, the blank 10 is shown herein for use with a particular socket 14 of a specific type of artificial leg 12, persons of ordinary skill in the art will readily appreciate that the teachings of the invention are in no way limited to use with that specific socket 14 and prosthetic device, or to any other particular environment of use. On the contrary, a blank 10 constructed in accordance with the teachings of the invention may be used with any type of socket used in any style of prosthetic device which would benefit from the advantages they offer without departing from the scope and spirit of the invention.

As best illustrated in FIG. 1A, the blank 10 comprises a sidewall 18 formed in a generally frustoconical shape having a rounded apex 19. It will be appreciated that the frustoconical shape illustrated in FIG. 1A is adapted for use with the particular socket 14 and artificial leg 12, and that the blank 10 may be formed in other shapes and sizes according to the particular size and type of socket. The sidewall 18 has an interior surface 20 which defines a recess 22 and an exterior surface 24. The sidewall 18 is preferably shaped and sized so that it snugly fits inside the socket 14, as described in greater detail below.

In accordance with certain aspects of the present invention, the blank 10 is formed of a thermoplastic material that is completely malleable at a low temperature. A low temperature, as used herein, is generally less than the temperature of boiling water (212° F.) and is preferably approximately 200° F. As a result, when the material is heated to the low temperature, the blank 10 may be molded into a different shape. The material also has a certain degree of stiffness upon cooling so that the blank 10 retains a molded shape and may be pulled out of the socket 14. Furthermore, the material has a sufficient flexibility after cooling to allow the material to be momentarily deflected or bent and yet substantially return to its exact molded shape. Accordingly, the material preferably has a flexural modulus between approximately 40,000 and 250,000 psi, and most preferably of approximately 180,000 psi, when cooled to room temperature. In a preferred embodiment, the blank 10 is formed of a low temperature thermoplastic nylon, such as the material marketed by Chesapeake Medical Supply under the name EXCEL-PLUS.

The blank 10 is used to form an impression of the socket 14, in accordance with additional aspects of the present invention. To prepare the socket 14 for the duplication process, an inside upper edge of the socket 14 is covered, such as with tape, to plug any holes or gaps formed in the socket 14 and to extend a proximal brim 26 of the socket in an upward direction. A powder is preferably applied to the socket 14 and tape to facilitate removal of the blank 10 after molding, as described below. While either talc powder or baby powder are preferred, almost any type of powder may be used. After the powder has been applied, the socket 14 is ready to receive the blank 10.

Figure 1B:
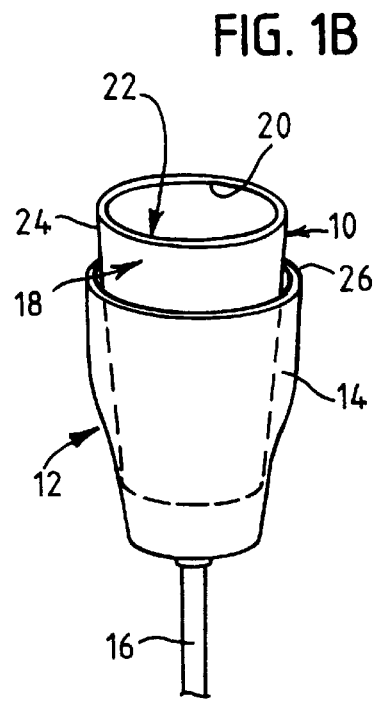
FIG. 1B is a perspective view illustrating the blank of FIG. 1A inserted into the socket.

The blank 10 is sized so that it closely fits inside the socket 14. To help achieve a snug fit, the blank 10 is preferably preheated before insertion, such as with a heat gun, until the blank material begins to be malleable. The pre-heated blank 10 is then inserted into the socket 14 as far as possible, as illustrated in FIG. 1B. The preheated blank 10 is slightly malleable, which allows it to be inserted as far as possible into the socket 14.

Figure 1C:
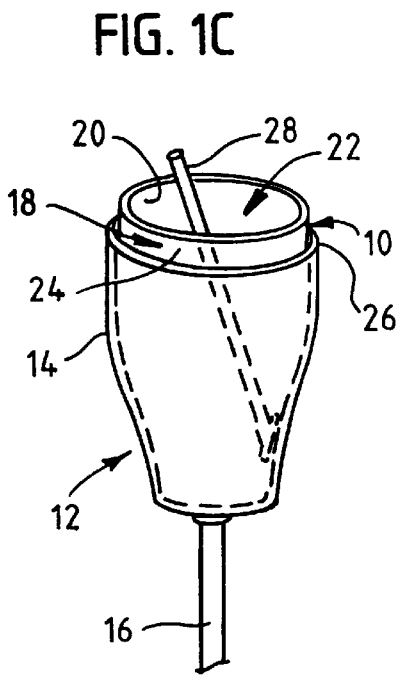
FIG. 1C is a perspective view illustrating the blank of FIG. 1A as it conforms to an inner surface of the socket.

Once the blank 10 is fully inserted into the socket 14, the blank 10 is heated to at least the low temperature so that the blank 10 is fully malleable. In the preferred embodiment, the blank 10 is heated by filling the recess 22 with heated water. For the preferred material, the water is heated to at least 165° Fahrenheit, and more preferably to approximately 200° Fahrenheit. The water not only warms the blank 10 to a sufficient temperature, but also creates a pressure which exerts an outward force on the sidewall 18, thereby urging the sidewall 18 toward the socket 14. To help mold the blank 10, a shaping tool, such as a long wooden spoon 28, may be inserted into the recess 22 to urge the sidewall 18 into all contours of the socket 14 (FIG. 1C). It is particularly important that the sidewall conforms closely to the proximal brim 26 of the socket 14 because this area is often critical for providing a comfortable fit for the user. The heat is applied for a sufficient period of time to allow the exterior surface 24 to fully conform to the socket 14. When using heated water, it has been found that a period of approximately 5 minutes is sufficient. The blank 10 must have a sufficient thickness to allow the sidewall 18 to stretch and deform to fit the contours of the socket 14. When using the preferred EXCEL-PLUS material, it has been found that a wall thickness of approximately 3/32" to 1/8" is sufficient for most applications. During the heating step, the exterior surface 24 of the blank 10 assumes a molded shape corresponding to the interior surface of the socket 14.

Other sources of heat may be used in accordance with the present invention. For example, the recess 22 of the blank 10 may be filled with heated sand, which also exerts outward pressure on the sidewall 18 in addition to heating the blank 10. Still other sources, such as a supply of hot air, may be used in combination with the shaping tool to mold the blank 10.

After the heating step, the molded blank 10 is cooled for a sufficient period of time so that the blank 10 hardens in the molded shape. In the preferred embodiment, the recess 22 of the blank 10 is filled with cold water for approximately 5 minutes. It will be appreciated that cooling sources other than cold water may be used in accordance with the present invention, such as cool sand.

Figure 1D:
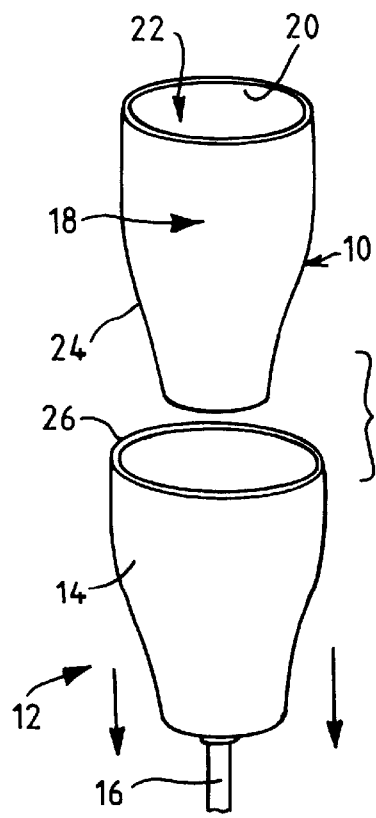
FIG. 1D is a perspective view illustrating the molded blank as it is removed from the socket.

After the molded blank 10 has been cooled, it is ready for removal from the socket 14. In the preferred method, an upper edge of the blank 10 is clamped and a downward force is applied to the artificial leg 12, such as at the supporting pylon 16, to pull the socket 14 away from the blank 10 (FIG. 1D). The material used to form the blank 10 has a sufficient flexibility which allows the blank 10 to deflect, thereby facilitating removal of the socket 14 from the blank 10. The deflections, however, are temporary and the blank 10 returns to the molded shape once it is removed from the socket 14.

After removal from the socket 14, the molded blank 10 may be used to form a new socket. To reinforce the blank 10 during the new socket forming process, the recess 22 of the blank 10 is preferably filled with plaster. In the most preferred embodiment, a two-step method is used to fill the recess 22. First, a slurry of plaster is deposited over the interior surface 20 of the blank 10. The slurry is allowed to set, thereby reinforcing the molded shape of the blank 10. After the slurry has set, the recess 22 is filled with plaster to form a solid center core. By first applying the slurry, the blank 10 is less likely to alter its shape under the weight of the plaster. A new socket may then be laminated over the blank 10 having the solid center core.

The above-described method may be quickly and easily altered to produce an impression having generally the same shape but a slightly smaller size than the original socket 14. To form the smaller size impression, a spacer having a desired thickness, such as a sock 30, is inserted in to the socket 14 before the blank 10 (FIG. 2). The sock 30 may be of varying thickness as needed, and typically has a three-ply or five-ply construction. The sock 30 covers the entire interior surface of the socket 14 and has an inner surface 32 defining a reduced socket recess 34. The blank 10 must therefore have a slightly smaller diameter to fit inside the reduced socket recess 34 of the sock 30. When the blank 10 is heated, it assumes a molded shape that corresponds to the inner surface 32 of the sock 30, which reduces the size of the recess 22 of the socket 14 by the thickness of the sock 30. The molded blank 10 is then used to form a new socket having a reduced size, thereby accommodating natural reductions in limb size without requiring the full socket fitting procedure.

To expedite the socket duplication process, it is anticipated that several blanks 10 of various sizes will be provided for common types and sizes of prosthetic devices. For artificial limbs attached below the knee, for example, blanks 10 having generally cylindrical shapes but different diameters can be used. For artificial legs used above the knee, the blanks 10 will have frustoconical shapes of various sizes, generally larger than the below the knee dimensions. In a similar fashion, blanks having other shapes and sizes may be provided for other prosthetic devices, such as symes (very long below knee), knee disarticulation, and arm prosthesis.

A blank 40 may also be used to make a direct impression of the remaining portion of the limb 41, as shown in FIGS. 3A–D. For this process, the remaining limb portion 41 should be prepared with a heat barrier, such as a thin wetted nylon, or a silicone suspension sleeve. The blank 40 is then heated until it is fully malleable and is inserted over the remaining portion of the limb 41, as illustrated in FIGS. 3A and 3B. An exterior surface 44 of the blank 40 is compressed so that the blank 40 is molded into the shape of the remaining limb portion 41 (FIG. 3C). The molded blank 40 is then removed from the remaining limb portion 41 (FIG. 3D).

When used to take a direct impression of the limb 41 as outlined immediately above, the molded blank 40 may be used for several different purposes. For example, the molded blank 40 may be filled with plaster to form a positive plaster impression, which may then be used to form a socket for a prosthetic device.

In addition, the molded blank 40 may be used as a liner 50 in a composite prosthetic device 52. The composite prosthetic device 52 includes an outer housing 54 into which the liner 40 is inserted. The outer housing 54 is formed of a material that is sufficiently rigid to support the liner 50 during use, and a supporting pylon 56 is attached to the outer housing 54. The liner 50 is more flexible than typical socket material to provide a more flexible fit with the remaining portion of the limb, which may increase the comfort of some prosthetic devices. The liner 50 is made from the low temperature thermoplastic nylon material, so that the liner 50 may be more easily molded to fit the remaining limb portion at a low temperature. In addition, the low temperature thermoplastic nylon material may be subsequently remolded to make adjustments in the size and fit of the liner 50, unlike conventional polyethylene flexible liners which are not remolded as easily as the low temperature nylon.

From the above, it will be appreciated that the present invention brings to the art a new and improved method and apparatus for forming a socket for a prosthetic device. According to certain aspects, a socket impression is formed using a blank formed of a solid material which is malleable at low temperatures. The blank is inserted inside the socket and heated so that the blank conforms to the shape and size of the socket. The blank is then cooled and removed from the socket. The blank material has a sufficient flexibility to allow the blank to deflect or bend slightly during removal. The molded blank may then be used to form a new socket. Accordingly, the present apparatus and method avoid the use of flowable materials which may leak through the original socket, thereby creating a mess and generating unnecessary costs. Furthermore, the original socket is not destroyed during the process. The blank is not susceptible to stretches or tears, and therefore it need not be repaired before forming the new socket thereon. After conforming to the socket, the molded blank accurately retains the molded shape.

In accordance with additional aspects of the present invention, a blank is used to form a direct impression of a remaining limb portion. The blank is heated until fully malleable and placed over the remaining portion of the limb. An outer surface of the blank is compressed so that the blank is molded into the shape of the limb. The blank is then cooled and removed. The molded blank may be used to form a positive plaster impression of the limb, or may be used as a liner incorporated into a composite prosthetic device.

The foregoing detailed description has been given for clearness of understanding only, and no unnecessary limitations should be understood therefrom, as modifications would be obvious to those skilled in the art.

What is claimed is:

1. A blank for forming an impression of an interior surface of a prosthetic limb socket, the blank comprising:

a side wall having an exterior surface sized for insertion into the prosthetic limb socket, the blank being formed of a thermoplastic material having a flexural modulus between approximately 40,000 to 250,000 psi;

the blank being malleable when heated to a temperature so that the exterior surface of the blank side wall is conformable to the interior surface of the prosthetic limb socket to obtain a molded blank shape;

the thermoplastic material being rigid yet temporarily deflectable when cooled below the temperature so that the blank side wall retains the molded blank shape when cooled yet deflects so that the blank having the molded blank shape is removable from the prosthetic limb socket.

2. The blank of claim 1, which the thermoplastic material is malleable when heated to approximately 200° F.

3. The blank of claim 1, in which the thermoplastic material comprises a low temperature thermoplastic nylon material.

4. The blank of claim 1, in which the side wall is initially formed in a generally frustoconical shape having a rounded apex.

5. The blank of claim 1, in which the thermoplastic material has a flexural modulus of approximately 180,000 psi.

* * * * *

UNITED STATES PATENT AND TRADEMARK OFFICE
CERTIFICATE OF CORRECTION

PATENT NO.   : 6,444,282 B1
DATED        : September 3, 2002
INVENTOR(S)  : Lee A. Shirer It is certified that error appears in the above-identified patent and that said Letters Patent is hereby corrected as shown below:

Column 8,
Line 18, please delete ", which" and insert -- , in which --.

Signed and Sealed this

Twenty-seventh Day of May, 2003

JAMES E. ROGAN
*Director of the United States Patent and Trademark Office*